(12) United States Patent
Paderni (10) Patent No.: US 6,302,854 B1
(45) Date of Patent: Oct. 16, 2001

(54) METHOD FOR COLLECTING FLUIDS

(75) Inventor: Valter Paderni, Sabbiadoro (IT)

(73) Assignee: CRB Nederland B.V. (NL)

( * ) Notice: Subject to any disclaimer, the term of this patent is extended or adjusted under 35 U.S.C. 154(b) by 0 days.

(21) Appl. No.: 09/242,394

(22) PCT Filed: Aug. 12, 1997

(86) PCT No.: PCT/EP97/04384

§ 371 Date: Apr. 20, 1999

§ 102(e) Date: Apr. 20, 1999

(87) PCT Pub. No.: WO98/07461

PCT Pub. Date: Feb. 26, 1998

(30) Foreign Application Priority Data

Aug. 16, 1996 (IT) .......................................... UD96A0159

(51) Int. Cl.[7] ...................................................... A61B 5/00
(52) U.S. Cl. ........................................... 600/573; 604/317
(58) Field of Search .................................... 600/573, 580, 600/584; 604/317

(56) References Cited

U.S. PATENT DOCUMENTS

| 5,053,025 | 10/1991 | Knippscheer | 604/317 |
| 5,342,328 | 8/1994 | Grossman et al. | 604/317 |
| 5,356,373 | 10/1994 | Dracker | 604/4 |
| 5,916,202 | * 6/1999 | Haswell | 604/356 |

FOREIGN PATENT DOCUMENTS 9203180    3/1992  (WO) .

* cited by examiner

*Primary Examiner*—Max Hindenburg
(74) *Attorney, Agent, or Firm*—Greer, Burns & Crain, Ltd.

(57) ABSTRACT

A method for collecting blood or fluids in general from a placenta or organ or body tissue through the cut end portion of the umbilical cord or of one or more vascularization vessels or outflow vessels of an organ or tissue, including the steps of connecting the cord, or vessel, to a collection apparatus and then applying pressure to the placenta, or organ or tissue.

9 Claims, 8 Drawing Sheets

METHOD FOR COLLECTING FLUIDS

BACKGROUND OF THE INVENTION

The present invention relates to a method for collecting blood or other fluids from an organ or tissue through a vessel. The method according to the invention is used in the biological, medical and veterinary field for diagnostic and therapeutic purposes and for research purposes to collect blood or other fluids from organs or parts of organs or tissues. In particular, the method according to the invention is used to collect placental blood, that is to say, the blood that is present in the placenta, during childbirth, directly after the birth of the neonate.

In the biological, medical and veterinary fields it is necessary to collect fluids, particularly blood, from organs or tissues or containers in general, both for diagnostic and therapeutic purposes and for research purposes. Two non-limitative examples are: 1. the collection of blood from masses of tumoral tissue, since the blood contained in the tumoral tissue is potentially useful for therapeutic purposes after appropriate treatment; 2. the collection of blood from the placenta during childbirth directly after cutting the umbilical cord. In this second case, the blood is useful since it contains stem cells, which are hematopoietic precursor cells, that is to say, cells which are capable of reconstituting the hematopoietic system and therefore can be used, if the need arises, for transplanting to the same donor or to another compatible recipient.

The procedures currently used to collect placental blood from an umbilical cord are described hereinafter as a typical example of the recovery of fluids from an organ; it is important to note that the reference to this practice is not limitative and is merely an example of situations in which it is necessary to collect blood or another fluid from tissues, organs or other containers in general.

Placental blood from the umbilical cord is collected because it contains hematopoietic stem cells which can be used for transplants. To allow the collected blood and therefore the recovered cells to be truly and successfully usable, the following conditions must be met: 1. the largest possible amount of blood, that is to say, the highest possible number of cells, must be recovered; 2. the collected blood, which is fetal in origin, must not be contaminated by foreign cell populations, such as for example maternal cells; 3. during collection, contact of the blood with the outside (air or other potentially contaminated objects) must be minimized, or the collection procedure must occur in sterile conditions, possibly in a closed environment; 4. the possibility of human error must be minimized.

Steps of Collection a. Before Expulsion of the Placenta

Blood is currently extracted from the placenta in the medical field, both for diagnostic and therapeutic purposes and for research purposes, as follows: during childbirth, directly after the expulsion of the neonate, the umbilical cord is closed (clamped) in two points and cut in a point which is intermediate between the two closure points. After cutting, the cut end of the umbilical cord which is connected to the placenta protrudes freely from the mother's vagina and is available for collection operations. Typically, blood is collected in the period between the cutting of the umbilical cord and expulsion of the placenta. During this period, the flow of blood is ensured by the pressure generated by uterine contractions, which by compressing the placenta facilitate the outflow of blood through the umbilical cord.

b. After Expulsion of the Placenta

Only a small number of authors reports collection procedures which provide for cord blood collection after expulsion of the placenta by placing the placenta on a frame and collecting the blood by gravity. The limited use of collection after expulsion of the placenta is certainly due to the low yield of collection by gravity and to difficulty in handling the placenta, especially when the sterility of the collected blood must be guaranteed.

Collection Systems

Collection of placental blood from the umbilical cord in the medical field, both for diagnostic and therapeutic purposes and for research purposes, is currently performed with methods which can be traced back to two categories: "open-circuit" systems and "closed-circuit" systems. Both systems are used for collection both before and after expulsion of the placenta.

a. "Open-circuit" Systems

"Open-circuit" systems collect placental blood from the cut umbilical cord in containers which contain anticoagulant. This collection is performed by making the blood flow out directly into the collection container without connecting the end portion of the cord, which is placed loosely at the inlet of the container.

Advantages

The main advantage of this system is the absence of resistances to flow, since there are no bottlenecks or sudden decreases in cross-section of the cord and of its vessels.

A second advantage is that the three vessels which are present in the umbilical cord are simultaneously pervious.

Another advantage of the system is the possibility to express the umbilical cord during collection.

Disadvantages

Various scientific papers have demonstrated that "open-circuit" systems do not ensure sterility and are in fact associated with a particularly high incidence of microbial contaminations. The cut end portion of the umbilical cord in fact has a loose consistency, and since it is simply rested on the inlet of the collecting container it can easily escape from it, consequently contaminating said end portion in addition to losing blood, which contaminates the outside environment.

Furthermore, the system inherently (being an "open" system) collects both the blood that flows out of the vessels of the cord and potentially contaminated liquids which flow along the outer surface of the umbilical cord; in particular, the maternal blood which is abundantly present along the outer surface of the placenta flows along the cord and mixes with the blood of the umbilical cord.

This collection system furthermore exposes the blood to the air of the outside environment, thus facilitating contaminations by microorganisms which are present in the outside environment.

Another drawback is the constant need for an operator assigned to keeping the umbilical cord in the correct position, particularly if repeated maneuvers for expressing and cleaning the cord are performed.

b. "Closed-circuit" Systems

Collection is performed by venipuncture of the cut and clamped end of the umbilical cord, after accurately disinfecting the entry point of the needle. The blood is collected in one or more syringes or in donation pouches.

Advantages

With respect to "open-circuit" systems, "closed-circuit" systems reduce the risks of microbial contamination of the collected blood and do not require continuous cleaning and disinfection of the cord.

Another advantage is reduction of the contamination of the sample with maternal blood or other liquids which flow along the outer surface of the cord.

Disadvantages

"Closed-circuit" systems entail handling needles and therefore expose the operators to the risk of accidental punctures.

Furthermore, the needle inserted in the umbilical vein is not stably fixed to it and can easily come loose, also in view of the highly dynamic nature of childbirth; this problem is particularly felt if collection is continued even after expulsion of the placenta. Accordingly, the continuous presence of an operator is required to ensure the correct placement of the needle during the various steps of collection.

If the needle leaves its seat, blood contaminations and accidental punctures of the operator are possible, and repetition of venipuncture is furthermore required in order to continue collection.

Owing to the limited cross-section of two of the three vessels of the umbilical cord (the arteries), collection is feasible only on one vessel (the vein), consequently reducing the collection potential.

The flow of blood is also hindered by the sudden decrease in cross-section (the needle, no matter how large, can never have the same cross-section as the umbilical vein).

The needle is inserted in an intermediate segment of the umbilical cord, upstream of the closure region; stasis of the blood downstream of the insertion point, with a consequent tendency to clotting, is thus inevitable; moreover, the blood which remains downstream of the insertion point is not recovered.

SUMMARY OF THE INVENTION

The aim of the present invention is to provide an improved method over the prior art cited above, for collecting blood or other fluids from the placenta or other organs or tissues for medical, scientific or other purposes.

An object of the invention is to ensure maximum sterility of the sample by applying a procedure and using a closed-circuit apparatus which minimizes contact of the blood or fluid with potentially contaminated external factors or with the air.

A further object of the present invention is to make the procedure accessible even to personnel who are not specifically trained. The procedure furthermore allows to limit the risks of human error on the part of the operator and, by using the suitable apparatus, to minimize the risk of injury to operators, since no exposed sharp or pointed objects are used.

The above aims and objects, and other aims that will become apparent to those skilled in the art are achieved by a method for collecting blood from the placenta or another organ or tissue through the umbilical cord or a main vessel by means of a closed system which sequentially includes:

1. Cleaning and disinfection of the portion of umbilical cord or vessel which is involved in the collection. The cleaning and disinfection system can be conveniently coupled to the system for connecting the umbilical cord or vessel.

2. Cutting of the cord in a position which is suitable for subsequent coupling to the connection system. The cutting system can be conveniently coupled to the connection system of the umbilical cord.

3. Connection of the umbilical cord or vessel by means of a connection system, optionally of the closed type, which can in turn be connected to a collection container; the connection system optionally includes a system for mixing the blood or other fluid with anticoagulant or other fluid or substance immediately after it has flowed out of the cord or vessel.

4. Optional insertion of the placenta or other organ or tissue in containment means.

5. Application of positive pressure to the placenta. The pressure can be uniform or, as an alternative, uneven, rhythmic, intermittent, centripetal, displacing or of one or more kinds, combined in various manners in order to mobilize the fluids from the more peripheral regions toward the main efferent vessels.

6. Application of continuous or intermittent negative pressure, as required, to the connection or to the collection container in order to facilitate the outflow of blood or other fluids or to free the vessel from clots or other obstacles.

BRIEF DESCRIPTION OF THE DRAWINGS

Further characteristics and advantages of the invention will become apparent from a reading of the detailed description of preferred but not exclusive embodiments of the invention, illustrated only by way of non-limiting examples in the accompanying drawings, wherein.

DESCRIPTION OF THE PREFERRED EMBODIMENTS

Figure 1:
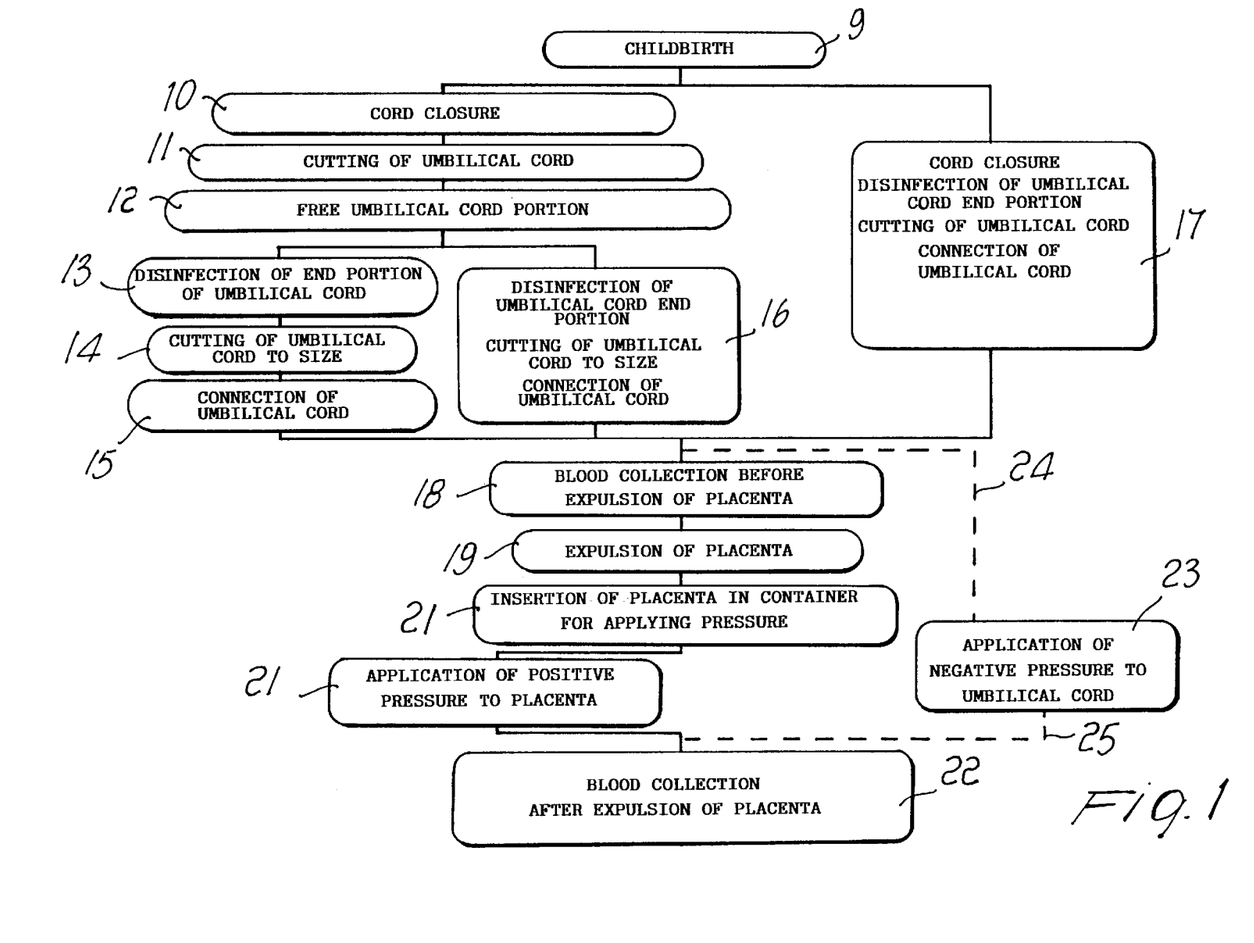
FIG. 1 is a schematic diagram of the procedure for collecting blood from the umbilical cord.

In the procedure according to the invention, after childbirth 9, the umbilical cord is closed (clamped) 10 in two points and then cut 11 in a median position between the two closure points. The portion of the umbilical cord that is connected to the placenta protrudes freely from the mother's vagina 12.

At this point, the end portion must be coupled to the collection container. The end portion of the umbilical cord is disinfected appropriately 13, optionally with a specifically designed disinfection system, is cut to size, if necessary, in order to adapt to the connection system 14, and is then coupled to the connection system 15. Said connection system (FIG. 2) is generally provided with suitable means for locking the cord, which prevents the cord from exiting from the system. The connection system is also provided with hermetic sealing means which isolate the cord portion from the outside environment at the inlet of said connection system, including any liquids which are present or flow on the outside wall of the umbilical cord. The sealing means are shaped appropriately and are constructed so as to not compress or choke the umbilical cord and in any case so as to avoid hindering in any way the collection of the blood or fluid. The connection system is then connected to the collection container, or the collection container can be an integral part of the connection system.

Figure 2:
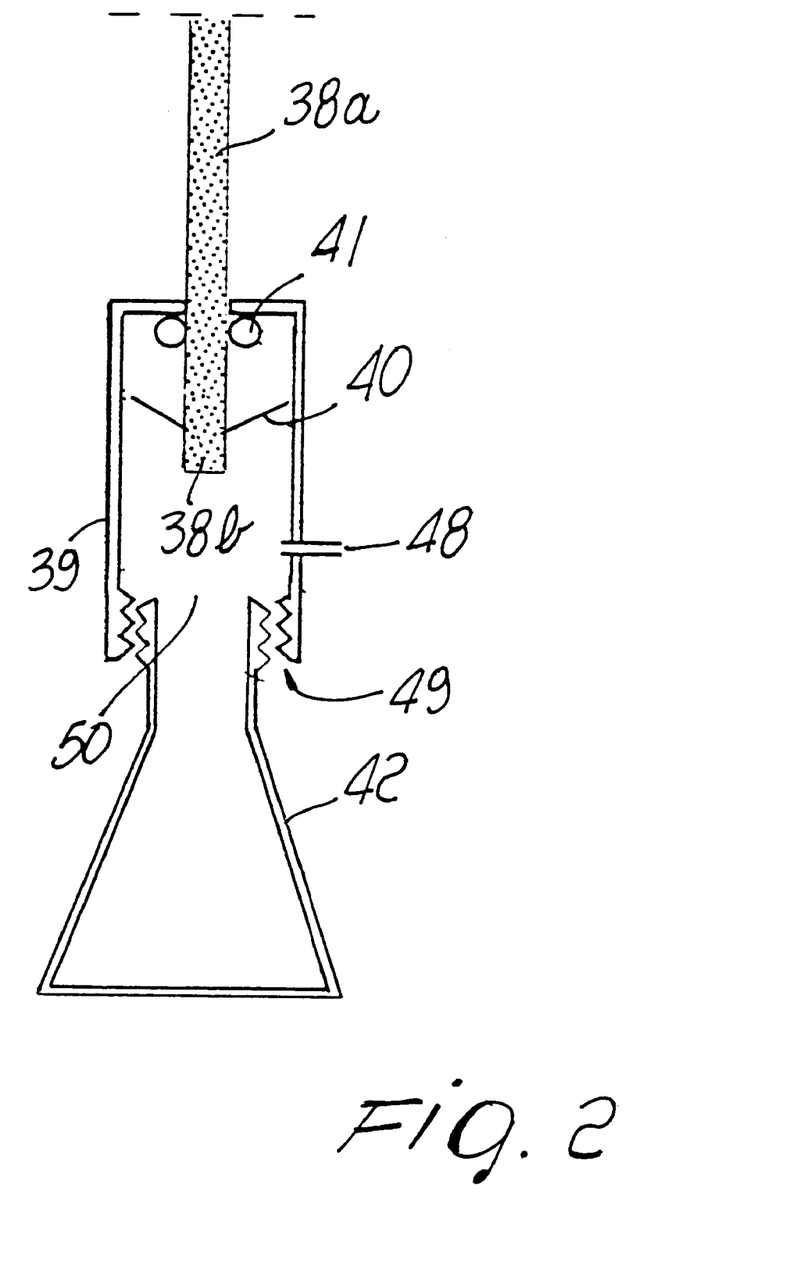
FIG. 2 is a view of a connection system according to a first aspect of the invention.

The connection system 39 which comprises means 41 for forming a seal on the umbilical cord which delimit a portion of the umbilical cord toward the placenta 38a and an open end portion 38b, means 40 for locking the cord, elements for connection to a collection container 49 so as to delimit a hermetic closed space 50 which comprises an optional access path 48 for applying pressure or for introducing anticoagulant fluid or another fluid or for drawing part of the blood.

The connection system, in one of its possible variations (FIG. 3), can also comprise in a single system, in addition to the vessel locking elements and to the sealing elements described above, cleaning and disinfection elements and cutting elements which are such that the operator, holding the end of the free portion of umbilical cord 12 with one hand, can disinfect the involved cord region, cut the cord to size and apply the connection system, which comprises both the locking elements and the sealing systems with a single operation 16.

Figure 3:
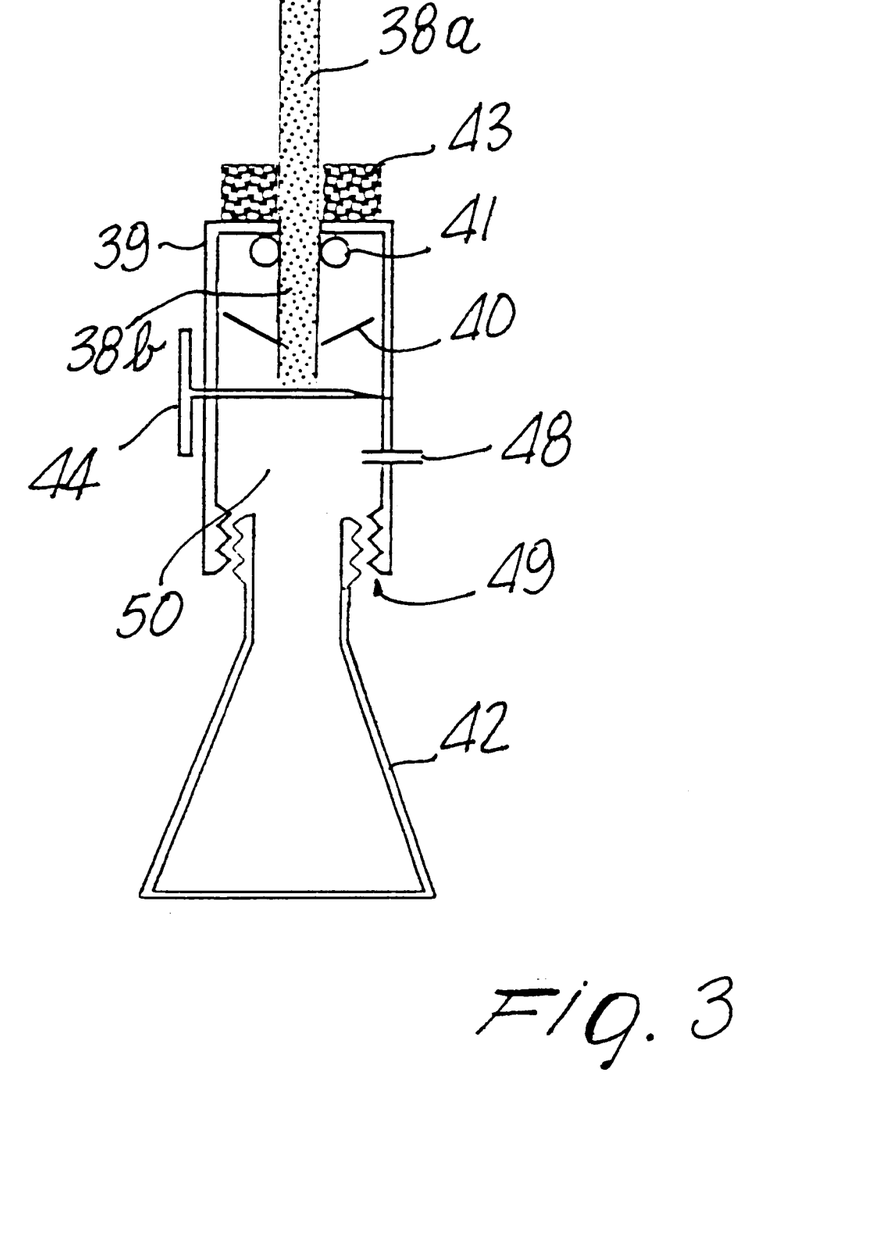
FIG. 3 is a view of a connection system according to a second aspect of the invention.
Figure 4A:
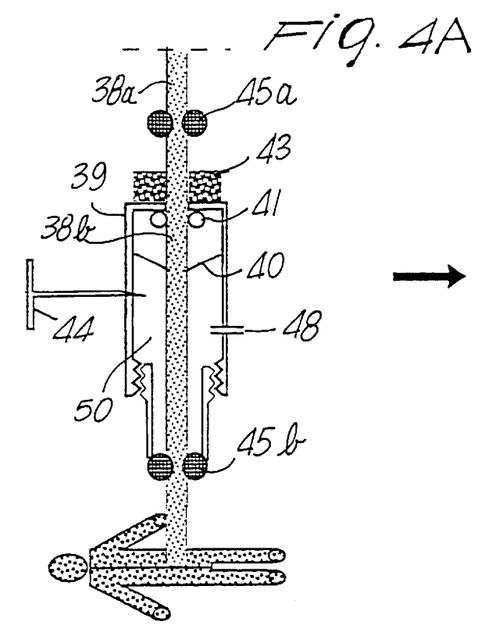
FIGS. 4A, 4B, 4C, and 4D shows the steps of the method using a connection system according to a third aspect of the invention.
Figure 4B:
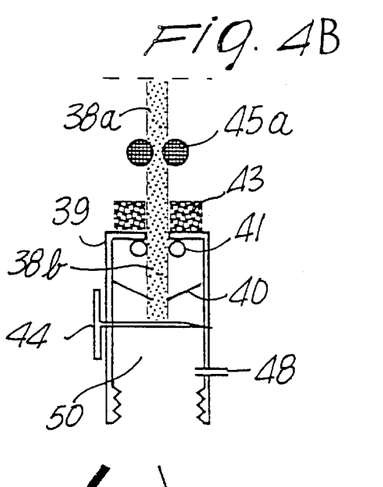
Figure 4C:
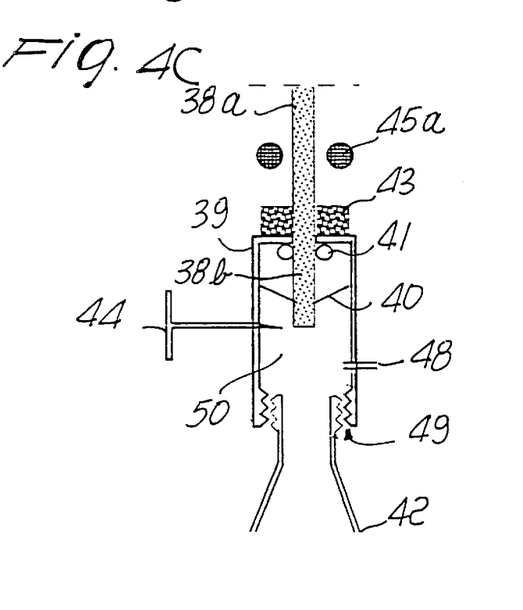
Figure 4D:
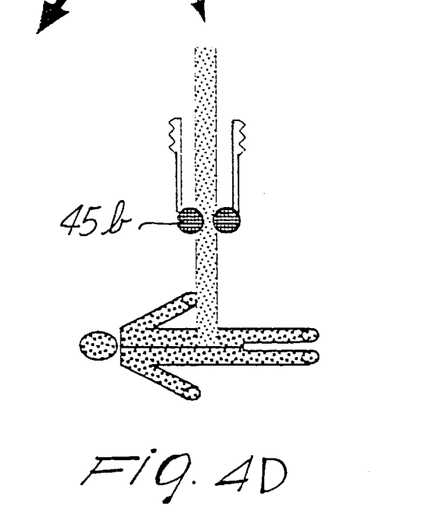

The connection system of FIG. 3 comprises means for disinfecting the end portion of the umbilical cord 43 and for cutting it 44.

An additional variation of the connection system 17, illustrated in a possible non-limitative embodiment in (FIGS. 4A, 4B, 4C, and 4D), can comprise the various elements required for disinfecting, cutting and locking the cord and hermetic sealing means designed to be applied before separating the neonate from the mother. In this case, the operator can use the same instrument to close, disinfect, cut and lock the cord and place the sealing elements 17 directly after the birth of the neonate.

The connection system of FIG. 4 comprises systems for closing or clamping 45 the umbilical cord upstream 45a and downstream 45b of the cutting point of said cord; the clamping elements downstream of the cut or toward the neonate 45b are temporarily connected to the system and, after cutting the cord, can be disconnected to leave room for the collection container 42.

Blood collection begins after applying the connection system. Before expulsion of the placenta, placental blood flows out owing to the pressure applied by uterine contractions to the placenta 18. After a variable period which lasts a few minutes, expulsion of the placenta occurs 19. During this step, the operator does not have to worry about the connection between the cord and the collection container, since the connection system has suitable locking means which ensure the stable connection between the cord, the connection system and optionally the collection container even during "dynamic" maneuvers such as expulsion of the placenta and transfer thereof to another location.

Figure 5:
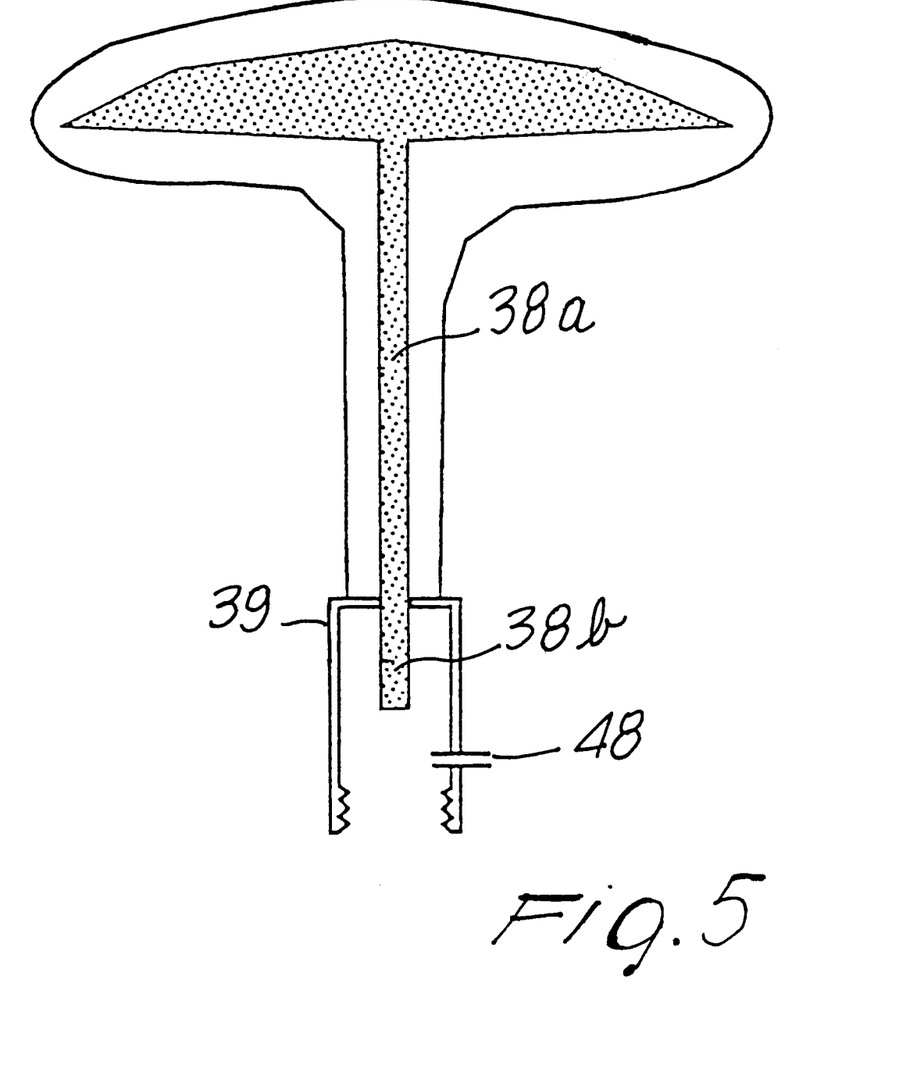
FIG. 5 is a view of the container of the placenta connected to the connection system.
Figure 6:
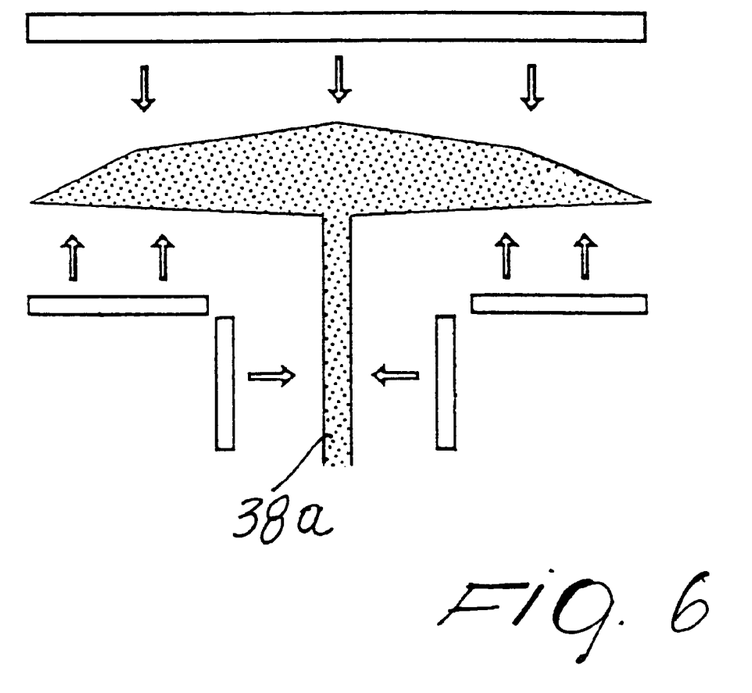
FIG. 6 is a schematic view of an apparatus for applying pressure to the placenta and to the proximal portion of the umbilical cord.
Figure 7:
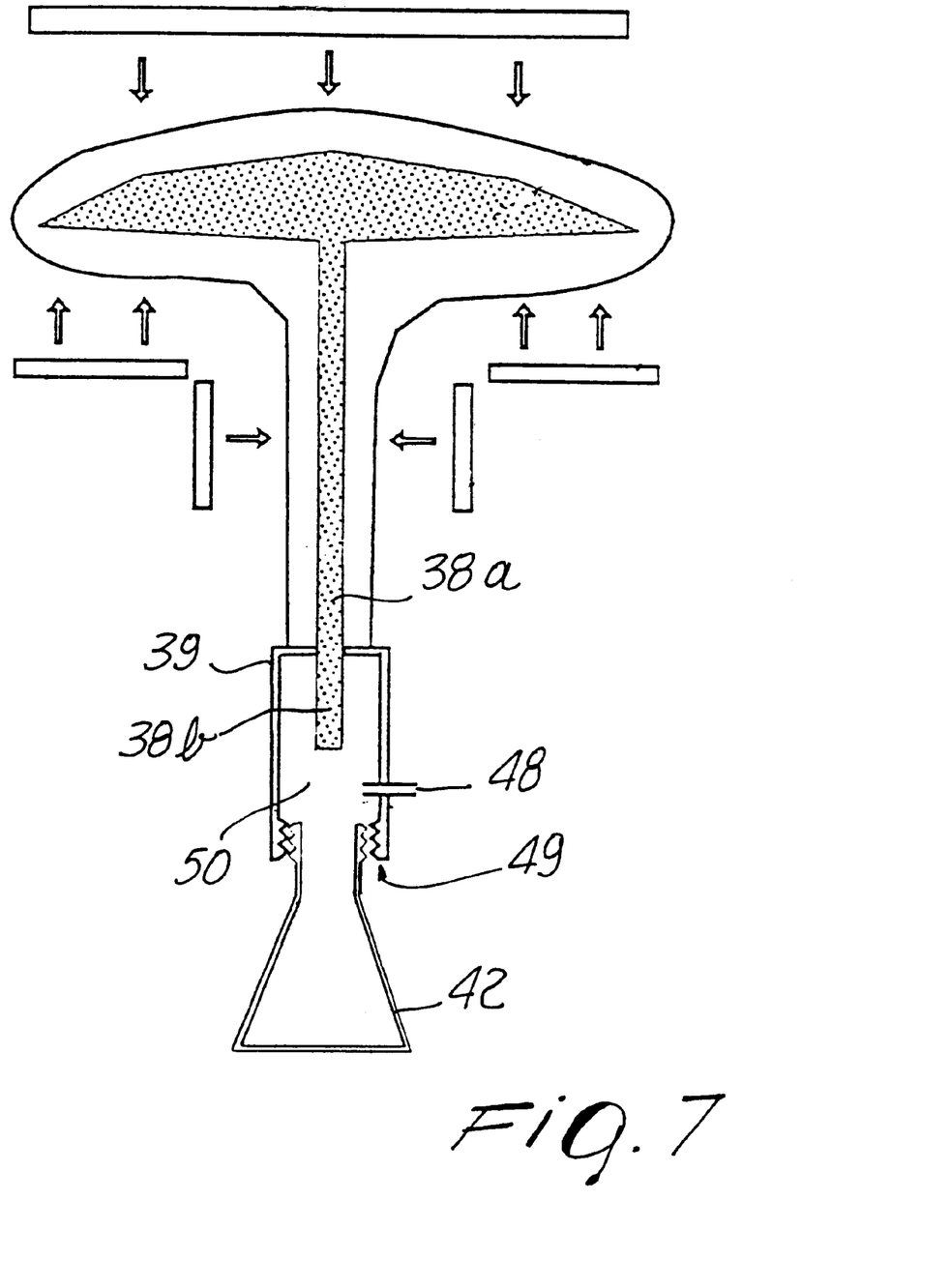
FIG. 7 is a view of a first embodiment of an apparatus for applying pressure to the placenta.
Figure 8:
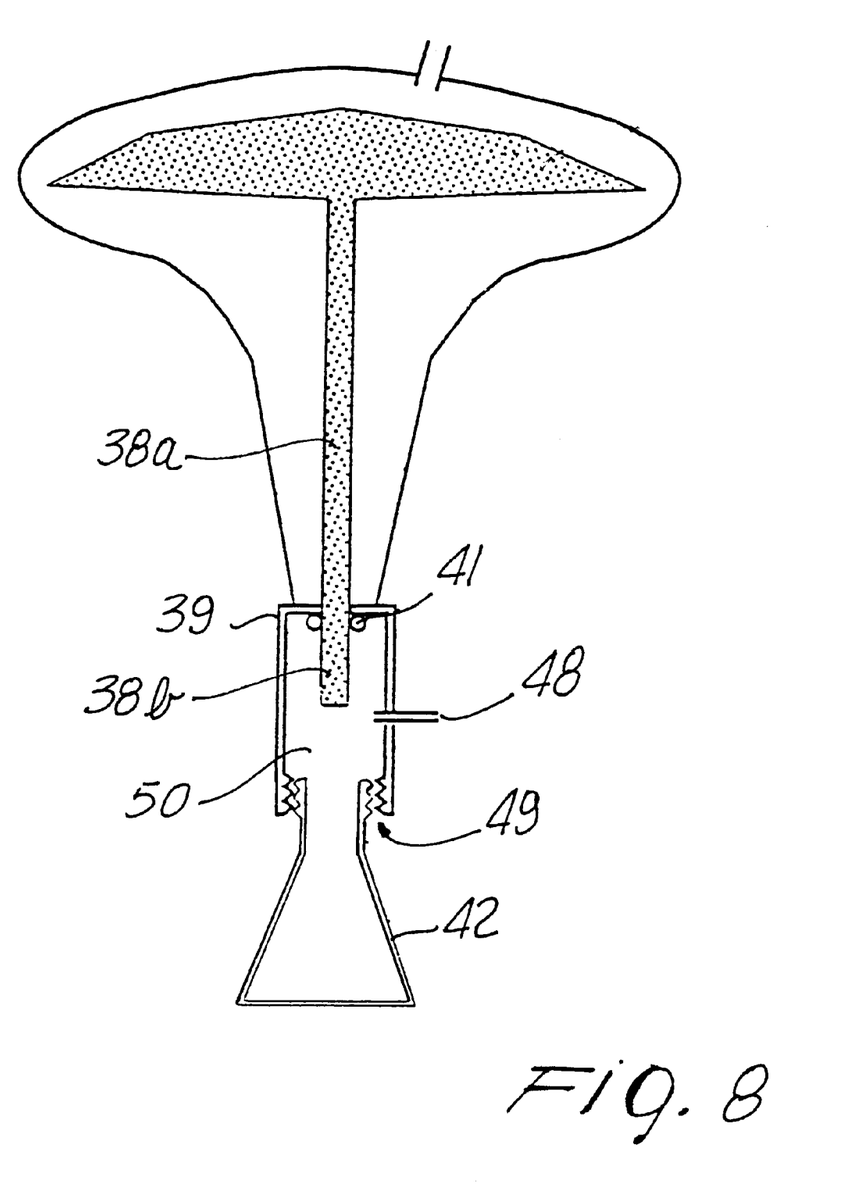
FIG. 8 is a schematic view of a second embodiment of an apparatus for applying pressure to the placenta.

After expulsion, the placenta is enclosed in a soft container (FIG. 5), optionally provided with an absorbent inner surface and an impermeable outer surface, which allows to avoid contaminating the outside environment and the operator 20 and is then subjected to pressure of various kinds by virtue of a suitable apparatus 21. During this second part of the collection 22, the flow of blood is ensured by the pressure applied appropriately by the specifically provided apparatus to the placenta. Said apparatus (FIG. 6) can be generally composed of elements which are suitable to apply pressures of various kinds to said placenta in suitable directions.

Another possibility for improving the yield of placental blood collection is the optional application of negative pressure to the point where the blood flows out of the umbilical cord, so as to generate a suction effect 23. The intensity of the suction is sufficient to facilitate the emptying of the cord and drainage of any obstacles, without however causing collapse of the vessels contained in the cord. The connection system in fact allows (FIG. 2, 3 and 4), by virtue of the hermetic sealing and pressure-tight systems, both on the umbilical cord and with the collection container, to create an enclosed space which can be pressurized. The negative pressure can be applied to the connection system both during the collection step before expulsion of the placenta 24 and during the second step after expulsion 25.

The procedure described so far then entails, after expulsion of the neonate, the cutting, cleaning, disinfection and connection of the cord with a suitable connection system which comprises suitable means for locking and isolating from outside the open end portion of the cord. The connection system can be, or already is, connected to a collection container with suitable sealing means. This is followed by a first collection of blood from the cord prior to expulsion of the placenta. During expulsion of the placenta, the cord remains coupled to the connection system and to the collection container, since the cord is firmly fixed and isolated from outside by virtue of suitable locking and sealing means, respectively. After expulsion, the placenta is inserted in a suitable soft container which has suitable hermetic closure means; said container can be an integral part of the connection system by being for example rolled up and packed on the outer edges of the connection system and activated when required by unrolling along the umbilical cord and then around the placenta to be finally closed at the apex of said placenta. At this point, the placenta contained in the container is subjected to a suitable pressure, such as to facilitate the flow of blood toward the outside through the umbilical cord in the enclosed space. Where necessary, in order to optionally further improve collection or eliminate obstacles or clots of the umbilical cord, it is possible to apply negative pressure to the open end portion of the umbilical cord by virtue of an access path provided in the connection system or in the collection container. By virtue of the sealing elements which are present in the connection system and isolate the enclosed space which accommodates the open end portion of the umbilical cord from the space that contains the placenta, it is also possible to apply the pressure directly in the sealed container of the placenta.

The described procedure allows, by means of a series of simple and safe operations, to maximize yield by virtue of sequential collection before and after expulsion of the placenta. The procedure also provides for the connection of the cord to a system which allows to keep all three vessels of the umbilical cord pervious, allowing them to contribute to the maximum yield of the collection. The operation provides for containment of the placenta and the cord from the initial steps, without using exposed pointed or sharp objects, ensuring the best possible safety of the operator. In the procedure, all the steps of collection are performed in a closed system, in which the blood does not make contact with the outside, thus preventing contamination of the sample. The procedure is easy and practical to use even for personnel who have not been trained specifically.

The procedure is very quick, can be partially automated, is designed to minimize the burden of the operator and can be applied in dynamic working conditions, such as operating rooms, delivery rooms etcetera.

In the system, as soon as the umbilical cord is cut, the placental portion of the umbilical cord from which the blood flows out is connected, after suitable disinfection, to the collection container by means of a closed connection system; said connection system eliminates the possibility of contaminating the blood, since it delimits a sterile closed region in which the blood passes from the umbilical cord to the collection container. The connection system, together with the container in which the placenta is placed, furthermore eliminate contaminations of the outside environment with placental blood, making the maneuver safe for the operator as well.

The system also allows to optimize the collection volume, since it combines collection from the vein and from the two arteries with the safety and practicality characteristics typical of a closed system. The combined use of the apparatus for applying positive pressure furthermore allows, for the first time, to recover volumes of fluid which are up to 100% higher than those obtained with currently used procedures.

What is claimed is:

1. A method for collecting blood or fluids from a placenta through a cut end portion of an umbilical cord, comprising the steps of:

clamping the umbilical cord of said placenta at two clamping points after the birth of a neonate;

cutting said cord in an intermediate point with respect to said two clamping points;

connecting the cord to a collection apparatus by coupling the cut end portion of the cord that arrives from the placenta to a collection container; and applying pressure to the placenta.

2. Method according to claim 1, comprising:
   immediately after the birth of the neonate, temporarily closing the cut end portion of the umbilical cord;
   disinfecting said cord;
   coupling said cord to a collection container.

3. Method according to claim 1, comprising:
   coupling the umbilical cord, directly after the expulsion of the neonate and without performing any cut, to a connection apparatus;
   locking, sealing, and disinfecting the cord in said connection apparatus.

4. Method according to claim 1, comprising applying said connection apparatus directly after the expulsion of the neonate, or before expulsion of the placenta, in order to start collection of the blood or fluids immediately after the birth of the neonate.

5. Method according to claim 4, wherein the connection apparatus remains coupled to the cord, before, during and after expulsion of the placenta.

6. Method according to claim 1, comprising connecting the connection apparatus to the collection container and simultaneously to the container of the placenta.

7. Method according to claim 1, comprising:
   applying negative pressure to the cut end portion of the umbilical cord by applying negative pressure to an enclosed space in which the open end portion of said cord is located.

8. Method according to claim 7, comprising: applying differentiated pressure to said enclosed space in which the open end portion of said cord is located.

9. Method for collecting blood or fluids in general from a placenta through the cut end portion of the umbilical cord, having a variable cross-section, with soft and elastic walls, and with a loose and easily collapsible consistency, comprising the steps of:

connecting the umbilical cord by means of a sterile connection apparatus, to a collection container, before expulsion of the placenta;

after expulsion of the placenta, applying a positive pressure such as to produce the outflow of the blood or fluid contained in the placenta.

* * * * *